(12) United States Patent
Talamantez et al.

(10) Patent No.: US 10,792,625 B2
(45) Date of Patent: Oct. 6, 2020

(54) METHOD AND APPARATUS FOR EXTENDING THE SHELF LIFE OF OZONATED WATER

(71) Applicants: Carla Talamantez, Bullhead City, AZ (US); John Strnad, Woodburn, OR (US); Bruce A. Thompson, Granite Bay, CA (US)

(72) Inventors: Carla Talamantez, Bullhead City, AZ (US); John Strnad, Woodburn, OR (US); Bruce A. Thompson, Granite Bay, CA (US)

( * ) Notice: Subject to any disclaimer, the term of this patent is extended or adjusted under 35 U.S.C. 154(b) by 201 days.

(21) Appl. No.: 15/917,604

(22) Filed: Mar. 10, 2018

(65) Prior Publication Data

US 2019/0275476 A1    Sep. 12, 2019

(51) Int. Cl.
  *B01F 3/04*    (2006.01)
  *A61L 2/18*    (2006.01)
  *B01F 5/04*    (2006.01)
  *B01J 19/08*    (2006.01)

(52) U.S. Cl.
  CPC ............ *B01F 3/0446* (2013.01); *A61L 2/183* (2013.01); *B01F 5/0413* (2013.01); *B01J 19/088* (2013.01); *B01F 2003/04886* (2013.01); *B01F 2003/04893* (2013.01)

(58) Field of Classification Search
  CPC .......... B01F 3/0446; B01F 2003/04886; B01F 2003/04893; B01F 2003/049; A61L 2/183; B01J 19/008; B01J 2219/0849; B01J 2219/0898; B01J 19/088; C02F 1/78
  See application file for complete search history.

(56) References Cited

U.S. PATENT DOCUMENTS

| | | | |
|---|---|---|---|
| 10,005,682 B1 * | 6/2018 | Hengsperger | C02F 1/78 |
| 2006/0021634 A1 * | 2/2006 | Liu | B01F 3/04503 |
| | | | 134/1.3 |

* cited by examiner

*Primary Examiner* — Lessanework Seifu

(57) ABSTRACT

A method and apparatus for significantly extending the shelf life of an inert gas infused fluid. Air that has been subjected to a high electrical potential corona and then mixed with a fluid in a constant differential pressure venturi is delivered to an improved container apparatus wherein an inert gas is infused into the fluid such that the resultant stabilized fluid demonstrates significantly improved usable life. Alternatively, an additive may be combined to provide application specific characteristics. The combination of the method and apparatus, taken together, provide substantially increased shelf life of an inert gas infused fluid.

11 Claims, 9 Drawing Sheets

METHOD AND APPARATUS FOR EXTENDING THE SHELF LIFE OF OZONATED WATER

This non-provisional application for utility patent claims 35 USC 119(e) priority based upon U.S. Provisional application 62/469,769, filed Mar. 10, 2017.

BRIEF DESCRIPTION

A method and apparatus for significantly extending the shelf life of an inert gas infused fluid is provided. Air that has been subjected to a high electrical potential corona and then mixed with a fluid in a constant differential pressure venturi is delivered to an improved container apparatus wherein an inert gas is infused into the fluid such that the resultant stabilized fluid demonstrates significantly improved usable life.

BACKGROUND OF THE INVENTION

Production and use of ozonated water has been known in the art for several centuries. First discovered in 1785 by the Dutch chemist Martinus van Marum, it has seen many uses throughout history. For example, as early as 1856 ozonated water has been used as a disinfectant in surgeries, the first documented ozone generator was developed in 1857 by Werner von Siemens, the first report of ozone used to purify blood occurred in 1870 by Dr. C. Lender, and in 1892 it was used as a treatment for tuberculosis.

Contemporarily ozonated water is used to kill viruses, bacteria, algae and fungi. Ozonated water breaks down harmful synthetic chemicals into less dangerous molecules and has been used to purify human blood. Biochemically, ozone disrupts the integrity of the bacterial cell envelope through oxidation of the phospholipids and lipoproteins. In fungi, ozone inhibits cell growth at certain stages. With viruses, ozone damages the viral capsid and upsets the reproductive cycle by disrupting the virus-to-cell contact with peroxidation. The weak enzyme coatings on cells which make them vulnerable to invasion by viruses make them susceptible to oxidation and elimination from the body, which then replaces them with healthy cells.

While there are numerous methods for producing ozonated water, contemporarily there are three methods in general use: hot spark, ultraviolet light and cold plasma. In the past hot spark production, more commonly referred to as coronal discharge, was used mostly for industrial applications, but modernly coronal discharge devices are available for personal application.

Ultraviolet and cold plasma are most commonly used for therapeutic work. Cold plasma will produce far greater quantities of ozone in a given time period compared to ultraviolet production. However, that is not to say that the ultraviolet method is not a useful for producing ozone. When a smaller, steady trickle of ozone is needed, the UV method might be the better choice, for example, for purifying water in a spa or hot tub.

No matter which method for production is used, ozonated water has a very short shelf life. [See for example *Characterization Of Water Quality Criteria for Ozonation Processes, Part II: Lifetime of Added Ozone*, J. Hoigné & H. Bader, *Ozone: Science & Engineering*, Vol. 16, Iss. 2, 1994.] Typically, efficacy dissipates in twenty to forty minutes depending on several variables. The result is that to realize the benefits of ozonated water, the production facility must be collocated, or at least within a short distance of the intended use site. This property of ozonated water is a distinct disadvantage.

Consider the use of ozonated water as a surface disinfectant, such as is commonly used in medical settings. In order to have sufficient quantities at the required concentration the water must be produced locally, using expensive equipment no more than twenty to thirty minutes from the point of use due to the current short shelf life of ozonated water. More realistically, since the depletion phenomenon is non-linear, the production facility should be no more than ten to twenty minutes from the use site. While this is feasible for major medical installations, it is a significant disadvantage for such facilities as hotels that need large quantities of surface disinfectant.

Since the shelf life of ozonated water is short, substitute products such as chlorine in various forms is used. In particular, chlorine bleach is a heavily corrosive fluid capable of irritating the eyes, skin and respiratory tract often by simply inhaling the gases its use emits. This inhalation has been noted to deteriorate the lungs and esophagus lining in addition to the scarring of the respiratory tract. Using chlorine bleach as a sanitizer, especially in a hospital setting where patients' immune systems are already compromised, can be harmful. As is known, chlorine is very harmful to the environment since its manufacture produces dioxin.

What would be desirable would be a method for substantially increasing the shelf life of ozonated water such that it could be processed in one location and used at a second location some distance away in time. What would be further desirable would be a plurality of transport containers of varying size and configuration such that a broader spectrum of users could be addressed.

SUMMARY OF THE INVENTION

A method and apparatus for significantly extending the shelf life of an inert gas infused fluid. Air that has been subjected to a high electrical potential corona and then mixed with a fluid in a constant differential pressure venturi is delivered to an improved container apparatus wherein an inert gas is infused into the fluid such that the resultant stabilized fluid demonstrates significantly improved shelf life. Alternatively, an additive may be combined to provide application specific characteristics including scent and flavor. The combination of the method and apparatus, taken together, provide substantially increased shelf life of an inert gas infused fluid.

The method of the present invention consists of mixing highly charged air and substantially particulate free water in a constant pressure differential venturi, then infusing the substantially particulate free water with O3 gas to stabilize the water by preventing a return to the H2O molecular state. The air is charged by exposure to a coronal discharge just prior to entering the venturi. Water is injected into the venturi at a known volume and the pressure across the venturi is held constant. Varying the pressure across the venturi can be used to control the concentration of O3 in the water. By infusing the aqueous ozone, or ozonated water with an inert gas to stabilize the water by preventing a return to the H2O molecular state, the shelf life of the ozonated water is significantly increased.

In an alternative embodiment of the process, one of a plurality of additives may be infused to the ozonated water. In this alternate embodiment, the additive may be a scent, for example, for a surface disinfecting fluid, or a flavor for human consumption. The additive is introduced to the ozonated water after exiting the venturi but prior to inert gas infusion. This is done to ensure that the final ozonated water has the correct molecular concentrations for a particular use. It will be recognized by those of skill in the art that the additive could be infused after the gas infusion without departing from the spirit of the invention, thus the introduction of the additive prior to gas infusion should not be read as a limitation on the scope of the invention.

As well as a novel process for creating ozonated water, stabilizing $O_3$ concentration over a long shelf life depends on maintaining the inert gas infused water under pressure, thus a plurality of use-specific containers has been created. Among these special purpose containers are small quantity and large quantity apparatuses. Small quantity containers include, but are not limited to, water bottles for human consumption and aerosol cans for surface disinfectant applications. Large quantity containers include, but are not limited to twenty to fifty-five gallon drums to be used as shipping containers for institutions.

Each of the above embodiments of the present invention is discussed in detail in conjunction with the drawings listed below. As will be evident, the method and apparatus of the present invention overcomes the disadvantages of the prior art devices and fulfills a long felt need for extended shelf life ozonated fluid.

DETAILED DESCRIPTION OF PREFERRED EMBODIMENTS

As described briefly above, the method and apparatus of the present invention significantly extends the shelf life of an inert gas infused fluid. FIGS. 1 through 6 set forth the present invention such that a person reasonably skilled in the art can make and use it.

Figure 1:
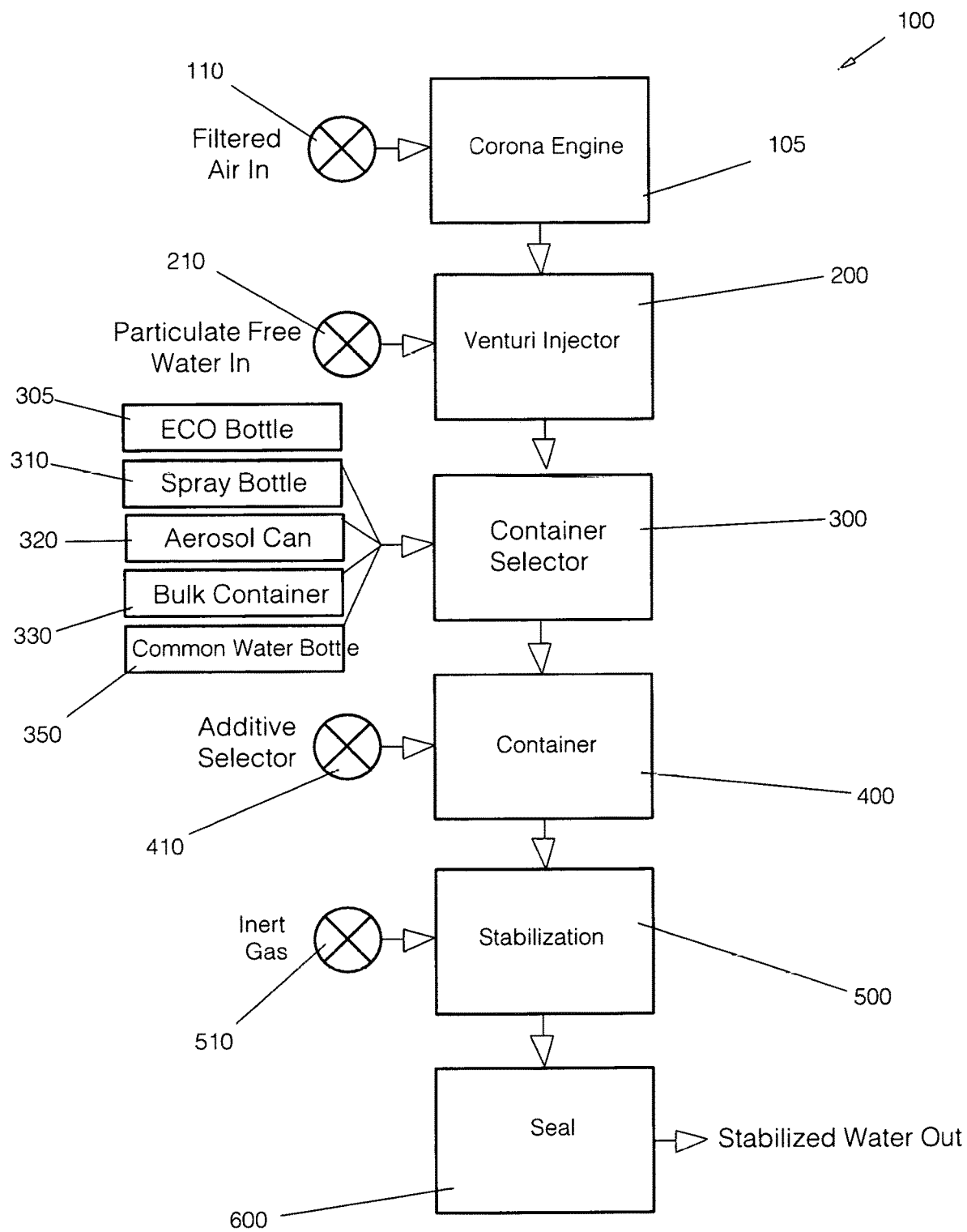
FIG. 1: is a block diagram of the apparatus of the present invention.

Beginning with FIG. 1, a functional block diagram 100 of the present invention is shown. Filtered Air 110 enters Corona Engine 105 at a predetermined pressure. Internal to the Corona Engine 105 the Filtered Air 110 is subjected to an electrical arc discharge which generates ozone gas. Since the input air is under some pressure, it flows into Venturi Injector 200 where it is mixed with substantially Particulate Free Water 210. As discussed in detail below, the pressure differential across the venturi is maintained at a constant level. By variation in the pressure differential across the venturi a precise concentration of ozone can be mixed into the water.

The mixture outflow from Venturi Injector 200 is placed into one of a plurality of special purpose containers via Container Selector 300. By way of example, but not meant as a limitation on the present invention, the special purpose container could be any one of an ECO Bottle 305, a Spray Bottle 310, an Aerosol Can 320, Bulk Container 330 or a Common Water Bottle 350. As will be set forth in the discussion of FIG. 3 below, ECO Bottle 305 is meant for small quantity use, for example, a water bottle suitable for human use. Spray Bottle 310 is suitable for use as a surface disinfectant dispenser, for example, cleaning of counter tops.

Aerosol Can 320, also for small quantities, may be useful in situations where a spray bottle is sub-optimum, for example cleaning under an overhanging surface where a spray bottle may not be used. Note that since aerosol technology is quite common, no detailed discussion is presented here; however, this is not to be taken as a limitation on the scope of the invention. In one instantiation of the present invention, the output spray is a fine mist, or fog. Due to the nature of the cold fog mist, the efficacy of the fluid is not impacted. The Bulk Container 330 is useful in shipping large quantities of fluid product, for example to medical institutions or hotels.

After the proper container has been selected, the fluid product is placed in Container 400. Recalling that any one of a plurality of containers may be used, an alternative embodiment of the present invention has the capacity to infuse an additive, for example a scent or a flavor. Additive Selector 410 is used to infuse one of a plurality of additives into the container at the same time as the fluid product is entering the container. By way of example, but not meant as a limitation on the present invention, the additive could be a pine scent or a "clean" scent.

The Stabilization function 500 infuses the fluid product with an inert gas such that the contents of the container will remain under pressure. It is the addition of pressure that significantly extends the shelf life of the ozonated fluid. Byway of example, the method and apparatus of the present invention increases the shelf life to one year with a retained effectiveness of 99.8 percent. This increase represents a shelf life improvement of over four orders of magnitude over the prior art.

An Inert Gas 510 is infused via any of the plurality of specialized containers set forth above. The inert gas used in a preferred embodiment of the present invention is $CO_2$, but as will be recognized by those of skill in the art, other inert gases could be used without departing from the spirit of the invention.

It will be noted that the larger containers have an input valve for use in infusing the inert gas. The inclusion of this valve is a significant improvement over contemporary containers for placing fluids under pressure since it provides an inherent environmental seal, eliminating the need for specialized equipment; however, it will be recognized by those of skill in the art that other filling methods, for example, top fill, could be used without departing from the spirit of the invention.

The final function block Seal 600 uses one of several sealing processes depending on which type of container has been filled with ozonated fluid. For example, if a bulk container is being used, a fill cap is put in place and an inert gas is used for initial pressurization. As discussed further below in conjunction with FIG. 5, the Bulk Container uses a combination of environmental sealing valves to ensure that the efficacy of the fluid does not degrade rapidly, thereby ensuring a significantly improved shelf life characteristic.

Figure 2A:
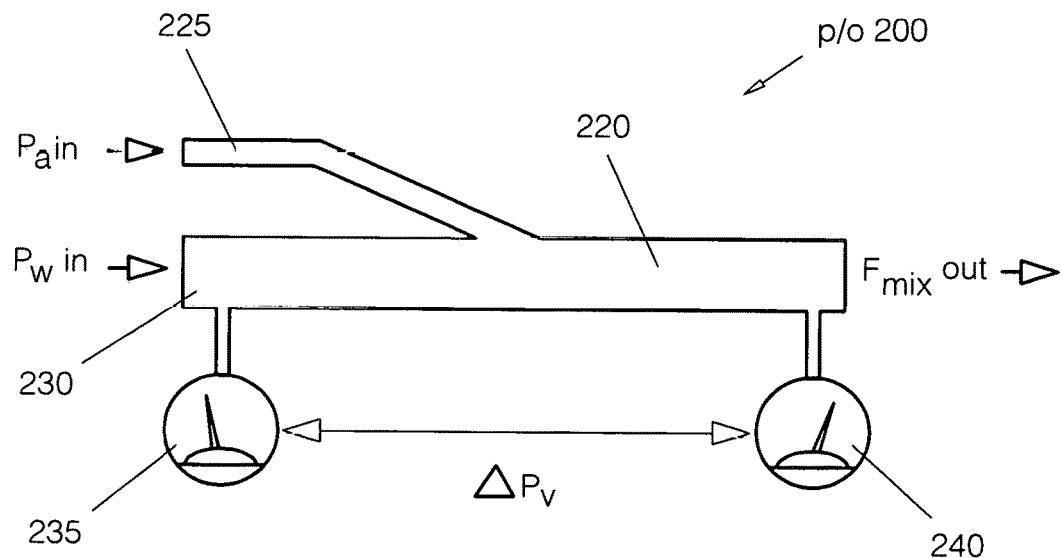
FIG. 2A: is a graphic representation of the improved venturi of the present invention.

Looking now at FIG. 2A, the venturi 200 of the present invention is shown. While venturi devices are well known in the art, it will be recognized by those of skill in the art that the venturi used for the present invention provides the ability to maintain a constant pressure differential $\Delta P_v$ across the device. This is critical since, with both the input air pressure Pain and input water volume $P_w$in held constant, it is the pressure differential $\Delta P_v$ that determines the concentration of ozone in the output fluid.

As shown in FIG. 2A, venturi tube 220 receives $P_a$in through air input port 225 and $P_w$in through water input port 230. $P_a$in is filtered air, either room air or oxygen enriched air, charged by a corona to a high electrical potential and is under some positive pressure while $P_w$in is substantially particulate free water in a known volume. The actual air pressure at the input to the venturi is of less importance than maintaining a constant pressure differential $\Delta P_v$ between the input of the venturi and the output of the venturi. In a preferred embodiment, the constant differential pressure $\Delta P_v$ is maintained at a minimum of ten (10) psi. This is controlled with a manual or self-adjusting restrictive valve so that the internal venturi pressure does not exceed, or is less than the liters-per-minute of ozonated air $P_a$in entering the mixing chamber.

As with the input air $P_a$in, the input water $P_w$in is under some positive flowrate. This flowrate is set such that the venturi pressure differential $\Delta P_v$ is not affected. As is known by those of skill in the art, both the air and water variables are able to be tightly regulated using contemporary methods, thus the precise control methods are not discussed in detail for clarity. For the preferred embodiment of the present invention, using room air, the venturi pressure differential $\Delta P_v$ is held at 14.7 psi, but as is known to those skilled in the art, other differentials could be used without departing from the spirit of the invention.

The air entering the venturi 220 has been subjected to a high voltage, alternating current to generate the ozone. Different voltage/frequency combinations will yield different ozone concentrations. Generally, AC voltage in the range of 9 to 20 kilovolts (KV) at a frequency between 6.4 and 22 kilohertz (KHz) will produce satisfactory ozone concentrations. In a preferred embodiment room air, or alternatively, oxygen enriched air is exposed to a corona in of 13 KV at a frequency of 1.0 KHz.

Pressure at the input of the venturi 220 is monitored by sensor 235 while pressure at the output of the venturi 220 is monitored by sensor 240. It will be recognized by those of skill in the art that both manual and automatic controls for these sensors are possible. In a preferred embodiment, the pressure differential ☐Pv is in the range of 10 to 30 PSI. Those skilled in the art will understand that other pressure differentials may be possible without departing from the spirit of the invention, thus the range given is for this preferred embodiment.

It is notable that through the filter system the static charge of the air is adjusted to increase or lower the static charge of the oxygen molecule. Also, through the filtration of the water, the charge level on the water may be controlled, assisting in the bonding of the air and water. This control is needed to accommodate local water properties being used at the time. Both the filtered air and filtered water assist in the bonding process. The more pure the air and the water, the better the bonding.

The result of the mixing in venturi 220 is an ozonated fluid product $F_{mix}$out that has a specific ozone concentration characteristic. The ability to vary the pressure differential delta $P_v$ is advantageous since it allows the present invention to provide different ozone concentrations for different applications. For the preferred embodiment of the present invention the concentration, or residual level of ozone, is in the range of 0.17 milligrams per liter (mg/L) to 5.6 milligrams per liter (mg/L).

Figure 2B:
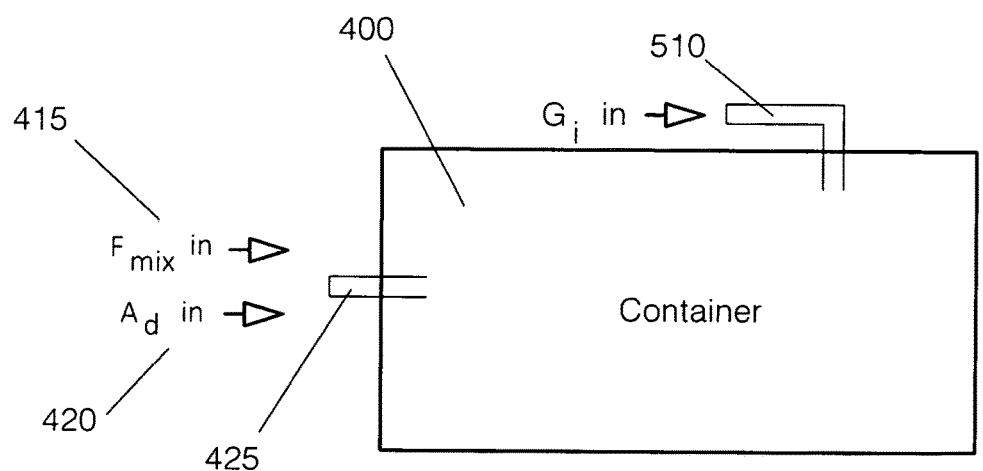
FIG. 2B: is a block diagram of the infusion process for the additive and inert gas of present invention.

FIG. 2B provides the details of the additive and gas infusion steps of the process. Container 400 receives $F_{mix}$in 415 via input port 425 and, if required, an additive $A_d$in via input port 425. Recall that an additive may be required for a specific product. If an additive is not required, then no $A_d$in input will be received by Container 400. Note that for the present invention the input port for both the additive, if needed, and the fluid mix is the same. This port could be a screw cap, a press fit cap, or some other capping method without departing from the scope of the invention. Filling a container with different fluids is well known in the industry, thus the details are not presented here, but in general, see https://www.youtube.com/watch?v=6ZKGUo9YmCA for an explanation.

With the combination of $F_{mix}$in and $A_d$in in container 400, an inert gas $G_i$in is infused under pressure via port 510. Input port 510 is of the type that self-seals upon disconnection of the input gas flow, allowing the contents of container 400 to remain under pressure. Input port 510 could be any of a number of self-sealing valves well known to those of skill in the art, but for the present invention the valve is of the Schrader type.

As discussed further below, the apparatus used to accomplish the infusion is designed to permit maximum molecular contact between the inert gas $G_i$in and the mixed fluid. As mentioned above, for the preferred embodiment of the present invention, the inert gas used is $CO_2$; however, other inert gases may be used without departing from the spirit of the invention. One benefit of the specialized containers is that they provide for this maximum molecular exposure, providing an optimized ozonated fluid product.

Figure 3:
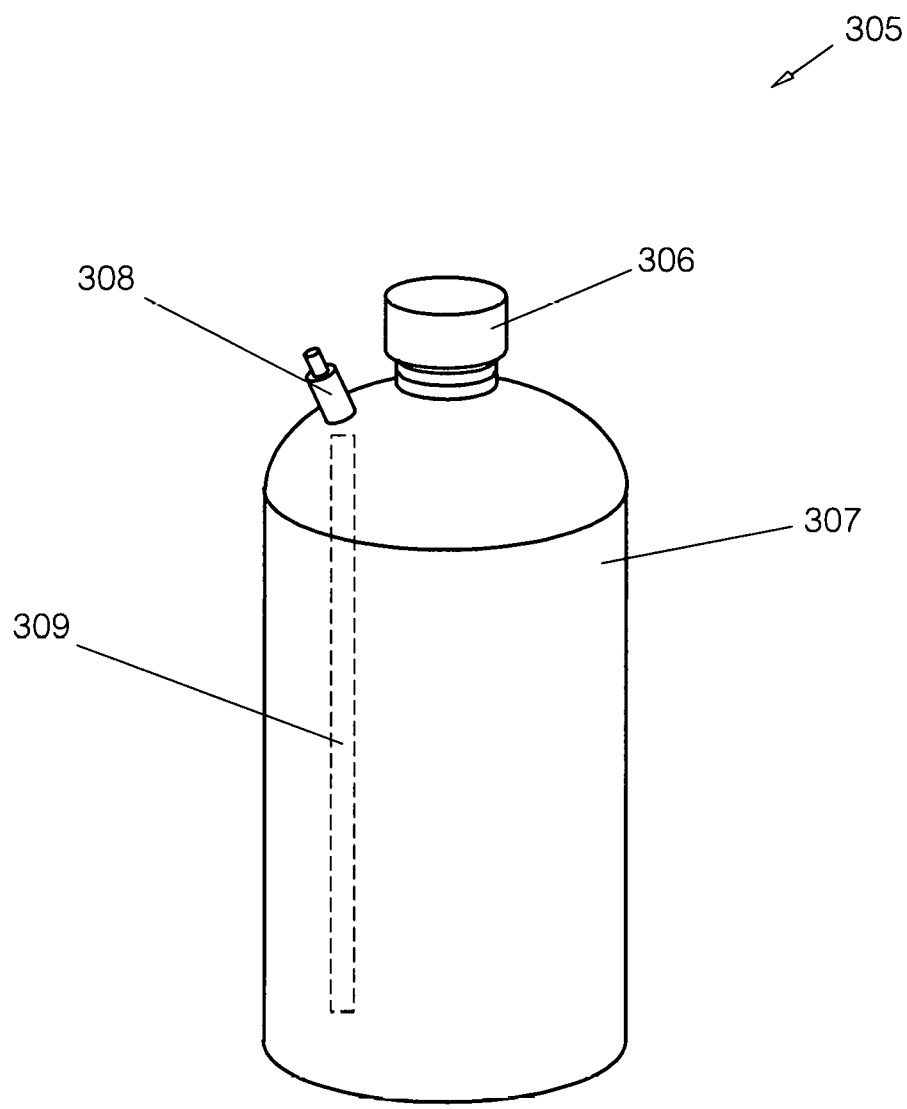
FIG. 3: is an isometric view of the special purpose small volume water bottle container of the present invention.

Turning now to FIG. 3, a first specialized container 305 is shown. Bottle body 307 is designed to hold pressure. Twist-off cap 306 is used to open the bottle 305 so that a user can access the contents and then reseal the bottle. In this example, bottle 305 is a water bottle such as those used during exercise or hiking, but as is known to those of skill in the art, bottle 305 could be used for any number of specific functions. Valve 308 and filler tube 309 are designed such that the incoming gas [$G_i$in of FIG. 2B] is forced to the bottom of bottle 305. In a preferred embodiment valve 308 is a Speedair Model A9150-BG-GRA Schrader valve; however, it will be recognized by those of skill in the art that other valves may be used without departing from the spirit of the invention. By forcing the gas to the bottom, it is required to rise through the entire contents, thereby maximizing molecular infusion. Valve 308 is used to infuse the gas and is monodirectional, such that once the gas has been infused, valve 308 seals shut maintaining the internal pressure, thereby significantly increasing the shelf life of the ozonated fluid.

Figure 4:
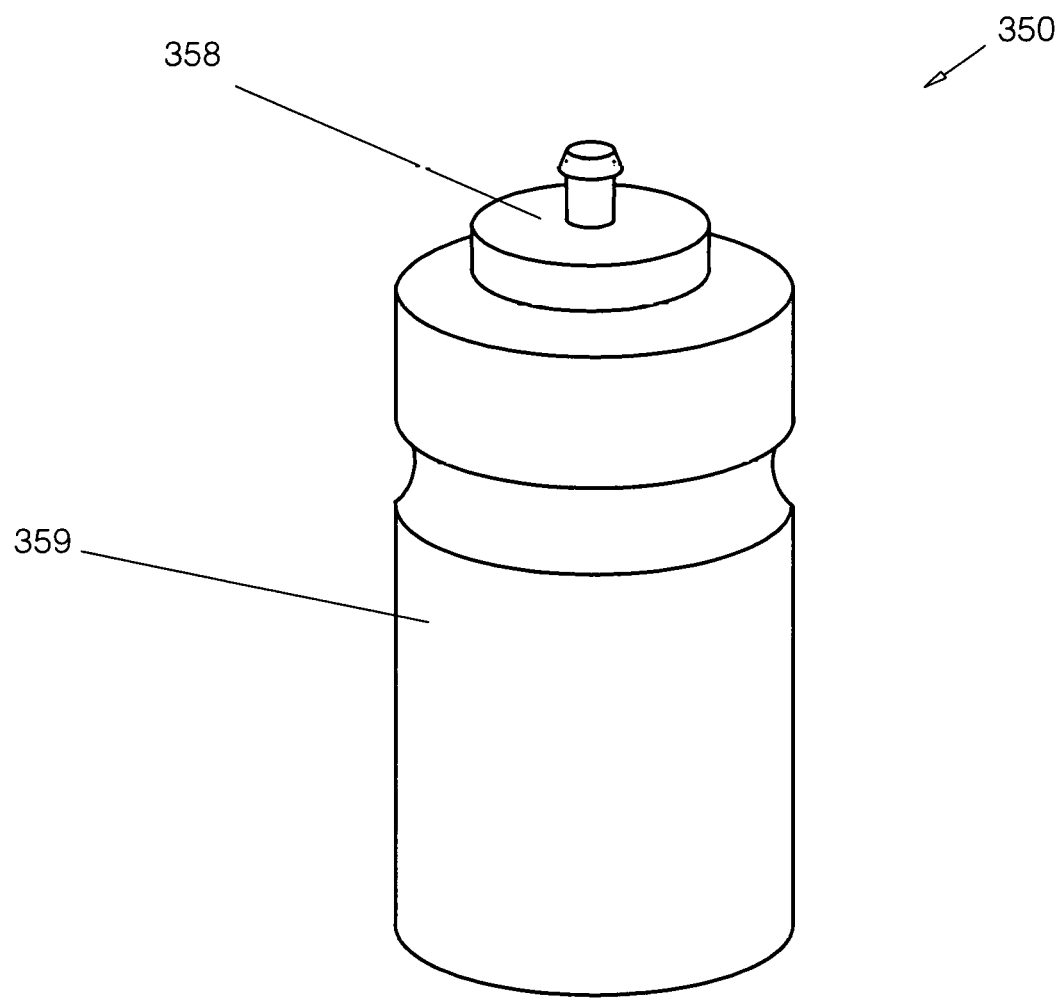
FIG. 4: is an isometric view of a common water bottle container of the present invention.

Looking now at FIG. 4, a common water bottle 350 of the type used by runners, cyclists, and others is shown. Bottle body 359 can be any material, but is commonly plastic. A cap 358 has a pull valve which may be opened or closed by a user. It will be noted that since the shelf life of ozonated water has been significantly increased by the method of the present invention, such common water bottles may be used.

Figure 5:
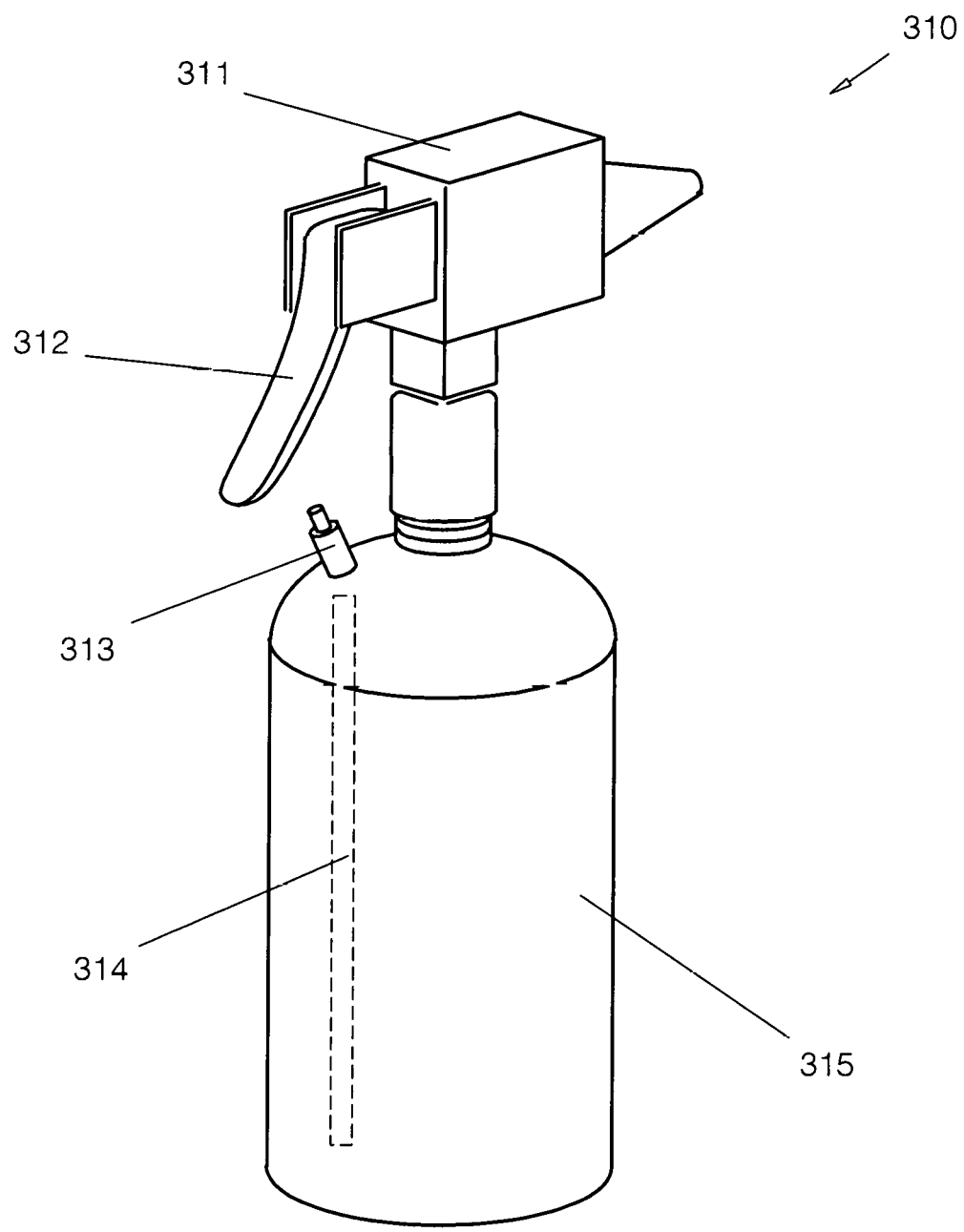
FIG. 5: is an isometric view of the special purpose small volume spray bottle container of the present invention.

FIG. 5 shows a second instantiation of a small quantity specialized container 310. In this instance bottle body 315 is designed to hold pressure similar to the bottle described in FIG. 3, but here the twist-off cap has been replaced by a lever operated spray head. When a user depresses lever 312, a valve inside valve body 311 opens, allowing the pressure inside bottle body 315 to force the ozonated fluid inside to spray out. Filler tube 314 and valve 313 operate in the same manner as was discussed in FIG. 2, so for clarity the detailed operation is omitted here. Of interest in this particular container is that advantageously no suction tube is required as is the case in contemporary spray bottles since the contents are under pressure and will spray out without suction.

Figure 6:
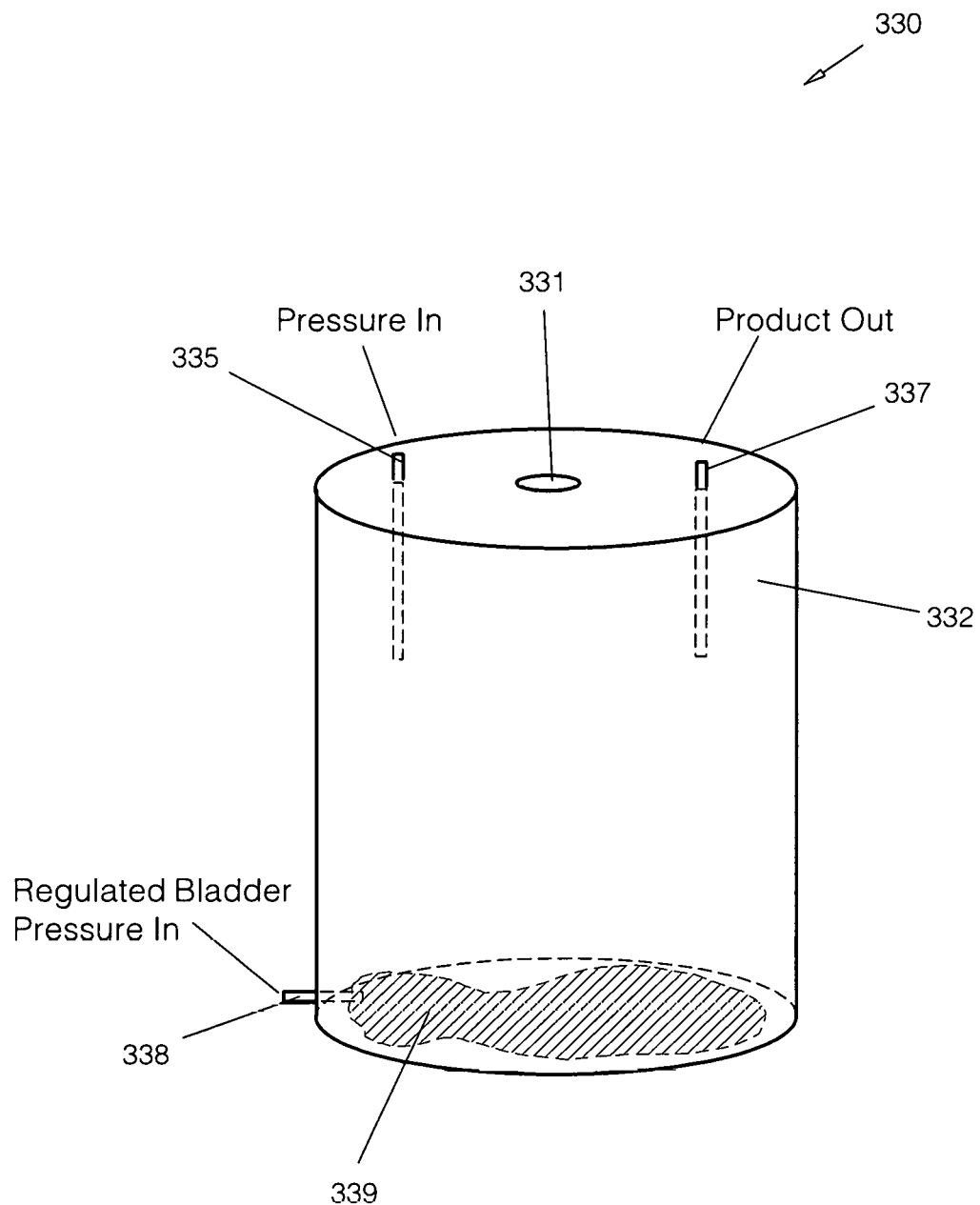
FIG. 6: is an isometric view of the special purpose large volume bulk shipping container of the present invention.

Shown in FIG. 6 is a bulk container 330 suitable for use with the present invention. The bulk container 330 could be any volume, but for purposes of this discussion, assume that it is 55 gallons, a typical bulk size for commercial fluids. The body 332 of the bulk container 330 is capable of holding pressure. Bulk ozonated fluid is put into the container 330 via filler cap 331 and then the cap is sealed. Initial pressurization occurs via valve 335, and as with other valves discussed previously, once the pressurization is complete the valve 335 seals shut. Valve 337 is used to remove ozonated fluid from bulk container 330.

As in known in the art, once a sufficient amount of fluid has been removed from bulk container 330, the internal pressure will drop. Recalling that it is the internal pressure that provides the extended shelf life of the ozonated fluid, bladder 339 may be inflated via valve 338 to compensate for the decreased internal pressure. Valve 338 is identical to the pressurization valves discussed above. As is known in the art, bladder 339 could be automatically adjusted through the use of an internal pressure sensor. An advantage of the bulk container 330 is that it may be used to transport large quantities of ozonated fluids while still maintaining extended shelf life.

Figure 7A:
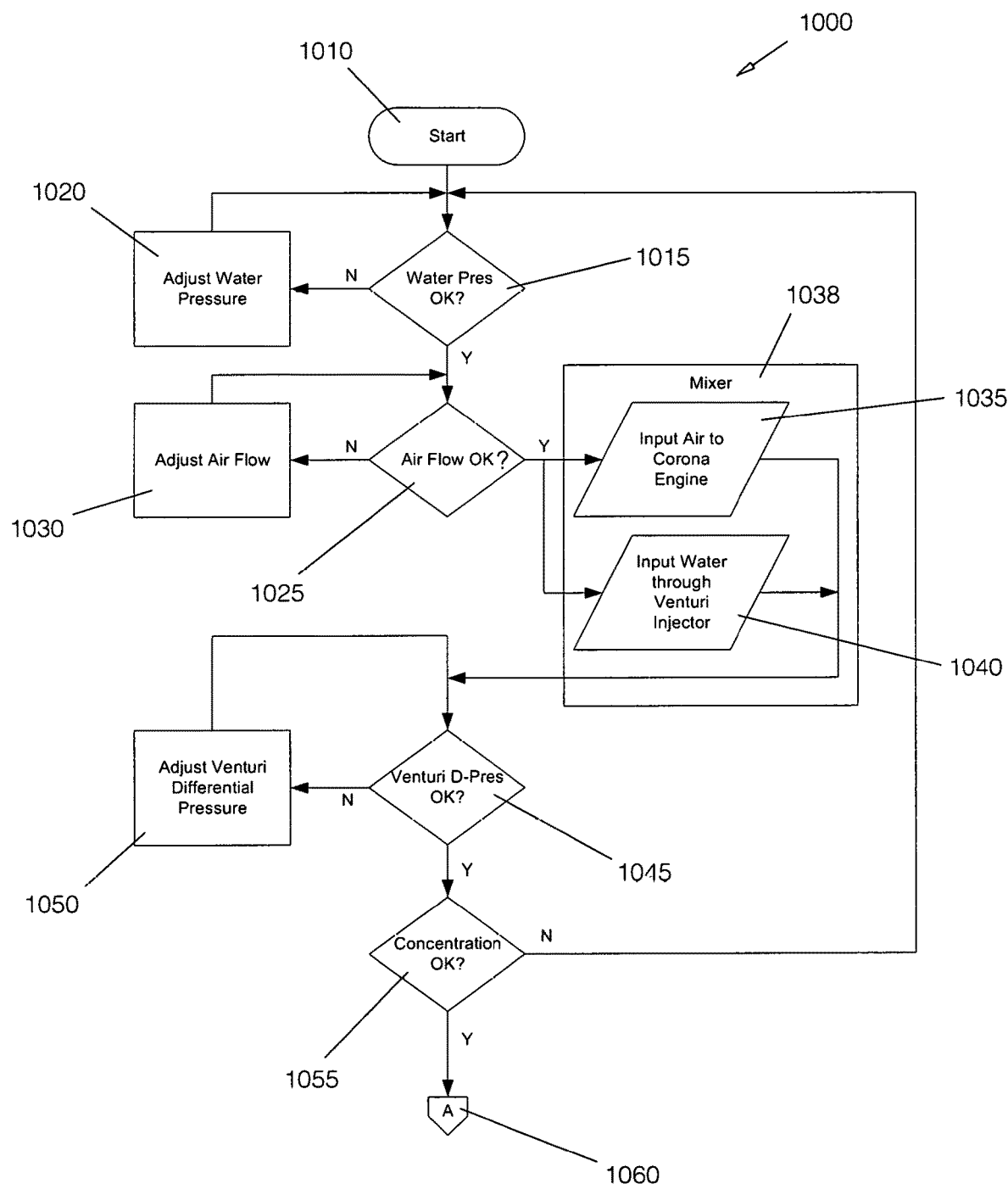
FIG. 7A: is a flowchart of the venturi steps of the present invention.
Figure 7B:
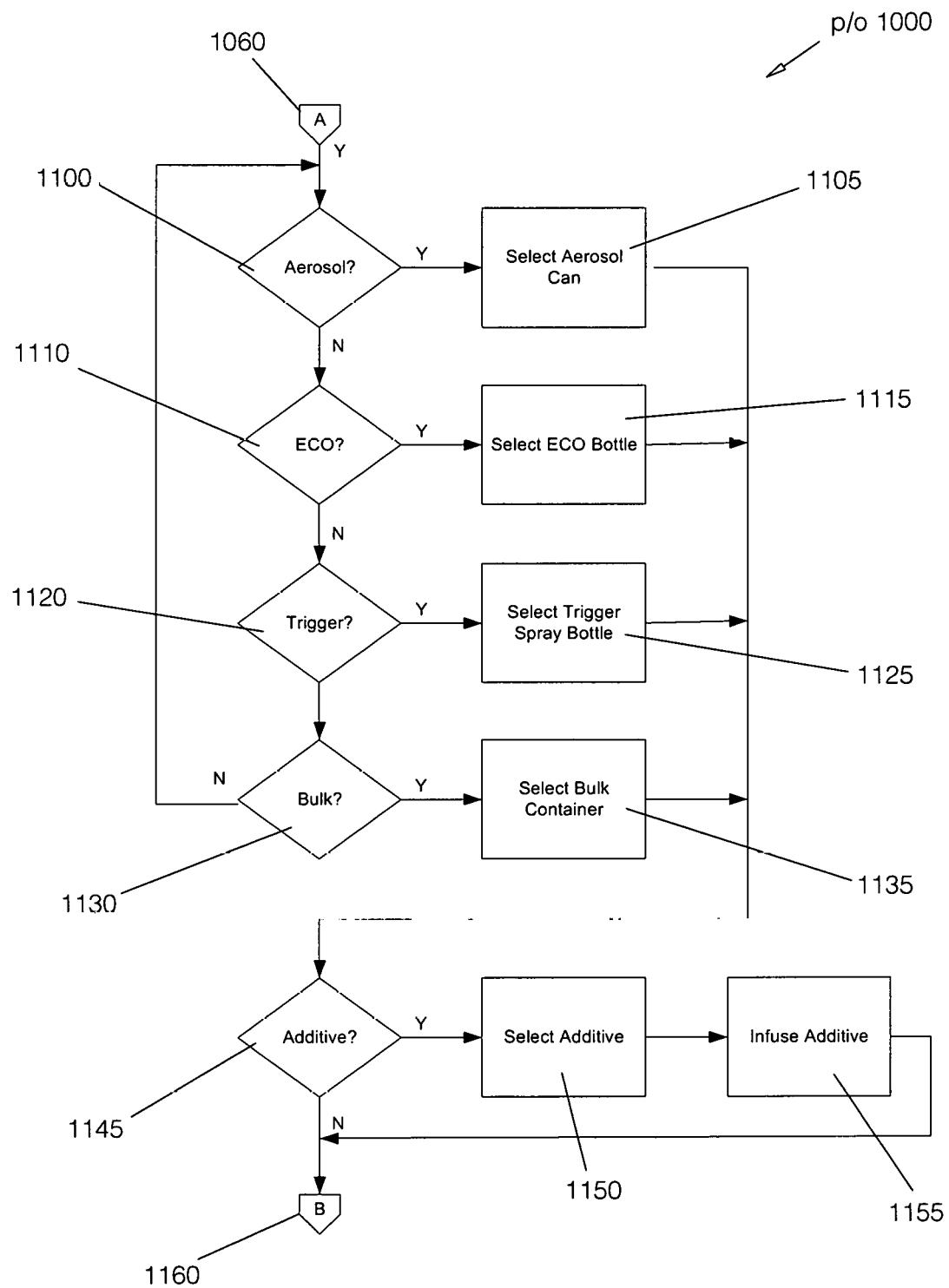
FIG. 7B: is a flowchart of the container selection and additive steps of the present invention.
Figure 7C:
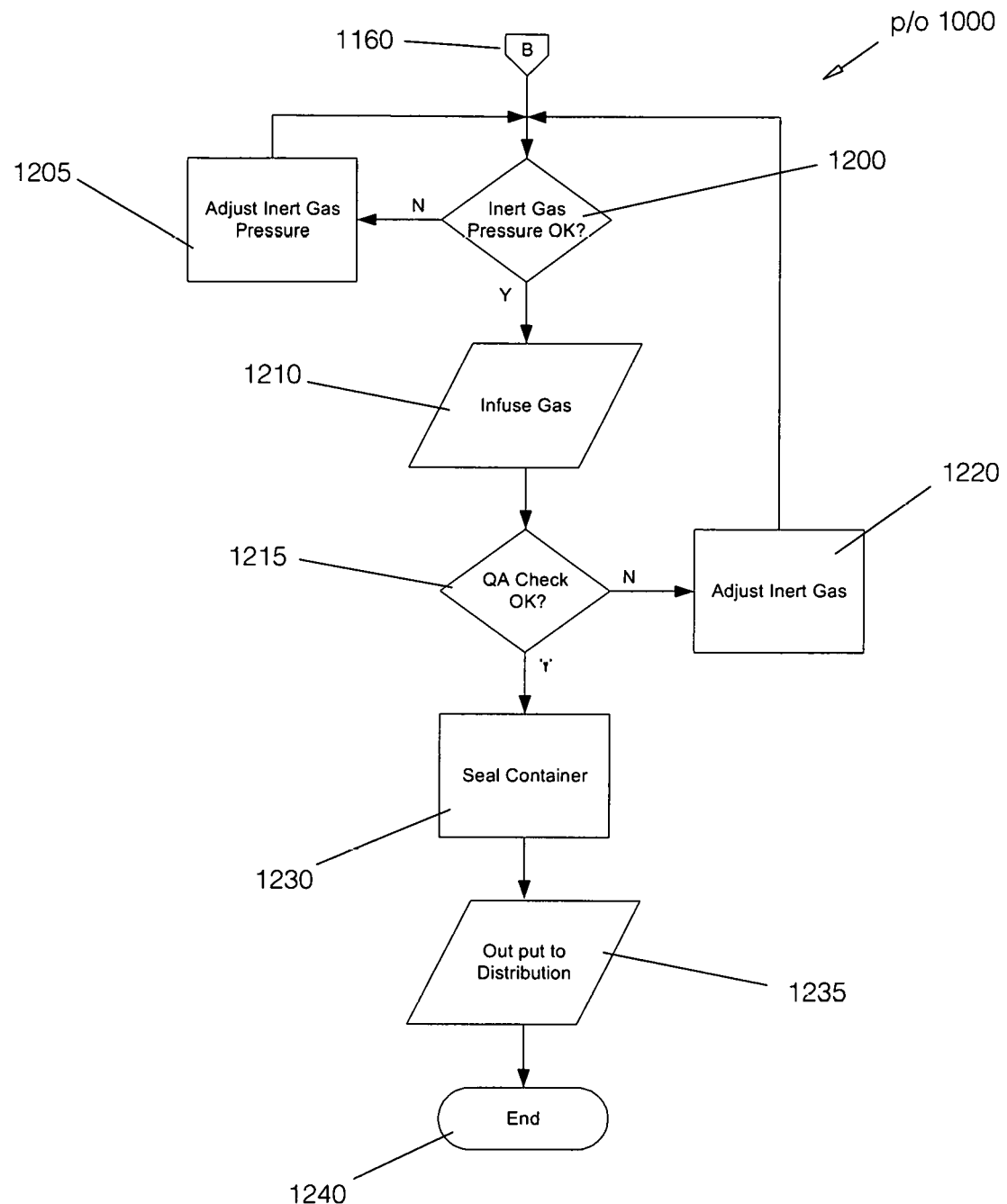
FIG. 7C: is a flowchart of the inert gas infusion steps of the present invention.

Keeping in mind that it is the combination of the method and apparatus of the present invention that provides the substantially increased shelf life of an inert gas infused fluid, the process of the present invention is discussed in detail via flowchart 1000 shown in FIGS. 7A, 7B and 7C. Beginning with FIG. 7A, the process is initiated at the Start step 1010. At Water Pressure OK step 1015 the process checks to ensure that proper water pressure is present at the input to the venturi injector, 200 in FIG. 1. If the pressure is incorrect, an adjustment is made at Adjust Water Pressure 1020, after which process flow returns to the Water Pressure OK step 1015. When correct pressure has been achieved, process flow passes to the Air Flow OK step 1025.

Assuming for the moment that the air flow is incorrect, an adjustment is made at Adjust Air Flow step 1030. Flow then returns to Air Flow OK step 1025. It will be understood by those skilled in the art that the adjustments could be manual or automatic without departing from the spirit of the invention.

If the air flow is correct, the filtered air is directed to a coronal discharge engine at Input Air to Corona Engine 1035. At the same time the substantially particulate free water enters the venturi mixer at Input Water through Venturi Injector step 1040. As can be seen, the combination of steps 1035 and 1040 form a Mixer 1038. As discussed in 1100, since the output product must be placed into some type of container, the process will continue to loop until a specific target container is selected. It must be noted at this point that, while a target container selection of four possible types is included for discussion, more or fewer containers could be used without departing from the spirit of the invention.

Once the differential pressure across the venturi is correct, a test is conducted to determine if the concentration level of ozone is proper for the specific product being made. As discussed above in conjunction with FIG. 2, for the present invention the concentration level, or residual level of ozone is held between 0.17 mg/L and 5.6 mg/L, plus/minus 0.1 mg/L. This occurs at Concentration OK step 1055. If the concentration is incorrect, flow loops back to Water Pressure OK step 1015. This is done since it could be any one of the three variables discussed that needs to be adjusted in order to assure proper ozone concentration in the venturi output. If the concentration level is correct, flow passes to the container selection sub-routine via off page connector A 1060.

FIG. 7B illustrates the container selection process starting at off page connector 1060. Beginning with the Aerosol step 1100, if the process product output is to be placed into an aerosol container, the yes path is followed to the Select Aerosol Can step 1105 and then to the Additive step 1145. If an aerosol container is not to be used, flow passes to the ECO step 1110. The ECO container is the reusable type such as that shown in FIG. 3 above. If the process product output is to be placed into an ECO container, the yes path is followed to the Select ECO Bottle step 1115 and then to the Additive step 1145. If an ECO container is not to be used, flow passes to the ECO step 1120.

At the Trigger step 1120, If the process product output is to be placed into a spray container, the yes path is followed to the Select Trigger Spray Bottle step 1125 and then to the Additive step 1145. If a spray container is not to be used, flow passes to the ECO step 1130. Finally, if the process product output is to be placed into a bulk container, the yes path is followed to the Select Bulk Container step 1135 and then to the Additive step 1145. If a bulk container is not to be used, flow passes back to the Aerosol step 1100. Since the output product must be placed into some type of container, the process will continue to loop until a specific target container is selected. It must be noted at this point that, while a target container selection of four possible types is included for discussion, more or fewer containers could be used without departing from the spirit of the invention.

Supposing for the moment that for the product being produced an additive is required. For example, a pine scent for a surface cleaning fluid or a citrus flavoring for a human water product. If such an additive is required, the Additive step 1145 passes process flow to the Select Additive step 1150. From there the Infuse Additive step 1155 infuses the selected additive directly into the container. Process flow now passes to the Inert Gas Pressure OK step 1200 via off page connector B 1160. It will be recognized that an additive selection tree similar in nature to the container selection tree could be used without departing from the spirit of the invention. Details of such a tree are well known in the art, thus are not discussed in detail here for clarity.

If the product being produced does not require an additive, process flow passes directly to the Inert Gas Pressure OK step 1200 via off page connector B 1160. Turning now to FIG. 7C, whichever container has been selected is now pressurized with an inert gas. This is done to significantly prolong the shelf life of the infused ozone. As noted above, the inert gas in a preferred embodiment of the present invention is $CO_2$. Byway of example, but not meant as a limitation, for a plastic bottle the pressure would be 40-55 psi at a standard room temperature of 73.4 degrees F., but in no case would exceed 100 psi based upon prior art in the industry. For any other particular container being used, the maximum psi will be based on the prior art in the industry.

At Inert Gas Pressure OK step 1200 a check is made to determine if the stabilizing gas to be used is at the correct pressure. In one embodiment of the process, as noted above, carbon dioxide gas is used for pressurization, but as will be recognized by those of skill in the art, other inert gasses could be used without departing from the spirit of the invention.

If the inert gas pressure is not correct, the no path is followed out of Inert Gas Pressure OK step 1200 to the Adjust Inert Gas Pressure step 1205. As was previously noted, the adjustments could be manual or automatic without departing from the spirit of the invention. Once the inert gas pressure is correct, process flow passes to the Infuse Gas step 1210 where the inert gas is infused into the product. At the QA Check OK step 1215, a test is done to assure that the product meets the specification for its intended purpose. If it does not, flow passes back to the Adjust Inert Gas step 1220 and then to the Inert Gas Pressure OK step 1200.

Assuming that the proper specifications have been achieved, the yes path is followed out of QA Check OK step 1215 to the Seal Container step 1230. Once the container is sealed, flow passes to the Output to Distribution step 1235, and from there the process ends at End step 1240. As can be seen, the process of the present invention provides a stabilized ozonated fluid with a significantly improved shelf life in a variety of containers. As will be recognized by those of skill in the art, while the embodiment described above uses ozonated water as its output, the process may be applied to other fluids without departing from the spirit of the invention.

A first advantage of the present invention is a significant extension to the shelf life of an ozonated fluid. Compared to contemporary methods for producing an ozonated fluid, the present invention provides a significant increase of several orders of magnitude in the shelf life of an ozonated fluid.

A second advantage of the present invention is that it has no environmental impact. This is so since ozone is an inert gas having no deleterious effects on the environment.

A third advantage of the present invention is the elimination of the need for the production equipment to be co-located with the use site.

A fourth advantage of the present invention is that a plurality of specific use containers may be used by the same production equipment.

A fifth advantage of the present invention is that compared to other disinfectants and sanitizers, the ozonated fluid produced by the method of the present invention can be used in lower quantities. This is so because, due to lower pH sensitivity, less reaction time is required to achieve sanitization.

A sixth advantage of the present invention is the reduced speed required for sanitation to take place. This is so because, as is well documented in the art, ozonated fluids require less dwell time, or contact time, to kill microorganisms.

A seventh advantage of the present invention is that it fulfills a long felt but unmet need for extended shelf life ozonated fluids.

What is claimed is:

1. A method for significantly extending the shelf life of an inert gas infused fluid comprised of:
    subjecting air to a high electrical potential corona:
    mixing said air under a first constant pressure with a fluid under a second constant pressure in a constant differential pressure venturi forming an air-fluid mixture:
    delivering said air-fluid mixture to a container, and:
    injecting an inert gas into said air-fluid mixture in said container such that the resultant stabilized fluid demonstrates significantly improved shelf life, said shelf life with a minimum of 30 to 40 days.

2. The method of claim 1 wherein an additive is infused into the air-fluid mixture at substantially the same time as said air-fluid mixture is placed in a container.

3. The method of claim 1 wherein said high electrical potential is between nine and twenty kilovolts.

4. The method of claim 1 wherein said high electrical potential is applied at between 6.4 and 20 kilohertz.

5. The method of claim 1 wherein said constant pressure differential is between 10 psi and 30 psi.

6. The method of claim 1 wherein said inert gas is carbon dioxide.

7. The method of claim 1 wherein said container is a spray bottle.

8. The method of claim 1 wherein said container is a water bottle.

9. The method of claim 1 wherein said container is a commercial drum with a capacity between twenty and fifty-live gallons.

10. An apparatus for significantly extending the shelf life of an inert gas infused fluid to a minimum of 30 to 40 days comprising:
    a constant differential pressure venturi, said constant differential pressure venturi having a controlled pressure air input port and a controlled pressure water input port and an output port:
    a control mechanism for maintaining a constant pressure differential between said controlled pressure air input port of said constant differential pressure venturi and said output port of said constant differential pressure venturi, and;
    a container, said container having at least two ports, the first of said ports for delivering one or more fluids to said container and the second of said ports for infusing an inert gas into said container such that said container remains under pressure after the inert gas source has been removed.

11. A system according to claim 1 or 10 for substantially increasing the shelf life of an ozone infused fluid.

* * * * *